(12) United States Patent
Biedermann et al.

(10) Patent No.: US 9,744,051 B2
(45) Date of Patent: Aug. 29, 2017

(54) SPACER FOR INSERTION BETWEEN TWO VERTEBRAE

(71) Applicant: Biedermann Technologies GmbH & Co. KG, Donaueschingen (DE)

(72) Inventors: Lutz Biedermann, Villingen (DE); Jürgen Harms, Karlsruhe (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 14/532,647

(22) Filed: Nov. 4, 2014

(65) Prior Publication Data

US 2015/0182349 A1      Jul. 2, 2015

Related U.S. Application Data

(63) Continuation of application No. 12/856,061, filed on Aug. 13, 2010, now Pat. No. 8,900,308, which is a
(Continued)

(30) Foreign Application Priority Data

Jul. 14, 2006    (EP) ..................................... 06014739

(51) Int. Cl.
*A61F 2/44*         (2006.01)
*A61F 2/46*         (2006.01)
(Continued)

(52) U.S. Cl.
CPC .............. *A61F 2/4465* (2013.01); *A61F 2/44* (2013.01); *A61F 2/4637* (2013.01);
(Continued)

(58) Field of Classification Search
CPC ...... A61F 2/44; A61F 2/442; A61F 2002/443; A61F 2002/4445; A61F 2/446
(Continued)

(56) References Cited

U.S. PATENT DOCUMENTS 5,211,664 A    5/1993  Tepic et al.
5,290,312 A    3/1994  Kojimoto et al.
(Continued)

FOREIGN PATENT DOCUMENTS

DE    195 09 317 A1    9/1996
EP      0 832 622 A2    4/1998
(Continued)

OTHER PUBLICATIONS

Office action for U.S. Appl. No. 11/645,228, dated Mar. 17, 2010, 8 pages.
(Continued)

*Primary Examiner* — Ellen C Hammond
*Assistant Examiner* — Christina Negrellirodrigue
(74) *Attorney, Agent, or Firm* — Lewis Roca Rothgerber Christie LLP (57) ABSTRACT

A spacer for insertion between two vertebrae includes a variable axial length and comprises a first member having a hollow interior and a tubular wall and a second member having a hollow interior and a tubular wall the second member being slidable within the first member in an axial direction for adjusting an overall length. At least the first member or the second member comprises an access opening in its wall, the opening having a size which is adapted for inserting bone grafts through the opening into the interior. The spacer further comprises a length adjustment structure being engageable with an expansion tool for telescoping the second member relative to the first member and a locking structure for fixing the axial length. The access opening, the
(Continued)

length adjustment structure and the locking structure are arranged so as to be accessible from the same side of the spacer. The spacer allows in situ filling of bone grafts into its interior and an improved handling.

21 Claims, 4 Drawing Sheets

Related U.S. Application Data continuation of application No. 11/776,409, filed on Jul. 11, 2007, now Pat. No. 7,803,191.

(60) Provisional application No. 60/830,809, filed on Jul. 14, 2006.

(51) Int. Cl.
*A61F 2/28* (2006.01)
*A61F 2/30* (2006.01)

(52) U.S. Cl.
CPC ............... *A61F 2002/2835* (2013.01); *A61F 2002/3024* (2013.01); *A61F 2002/3055* (2013.01); *A61F 2002/30125* (2013.01); *A61F 2002/30233* (2013.01); *A61F 2002/30367* (2013.01); *A61F 2002/30476* (2013.01); *A61F 2002/30507* (2013.01); *A61F 2002/30579* (2013.01); *A61F 2002/30601* (2013.01); *A61F 2002/30729* (2013.01); *A61F 2002/30772* (2013.01); *A61F 2002/30818* (2013.01); *A61F 2002/4475* (2013.01); *A61F 2002/4622* (2013.01); *A61F 2220/0025* (2013.01); *A61F 2220/0033* (2013.01); *A61F 2230/0008* (2013.01); *A61F 2230/0069* (2013.01)

(58) Field of Classification Search
USPC .............. 606/246–249; 623/17.11–17.16
See application file for complete search history.

(56) References Cited

U.S. PATENT DOCUMENTS

| | | | |
|---|---|---|---|
| 6,015,436 A | 1/2000 | Schönhöffer | |
| 6,176,881 B1 | 1/2001 | Schar et al. | |
| 6,193,755 B1 | 2/2001 | Metz-Stavenhagen et al. | |
| 6,200,348 B1 | 3/2001 | Biedermann et al. | |
| 6,447,543 B1 | 9/2002 | Studer et al. | |
| 6,524,341 B2 | 2/2003 | Lang et al. | |
| 6,616,695 B1 | 9/2003 | Crozet et al. | |
| 6,783,547 B2 | 8/2004 | Castro | |
| 6,902,579 B2 | 6/2005 | Harms et al. | |
| 7,674,296 B2 * | 3/2010 | Rhoda | A61F 2/44 623/17.11 |
| 8,182,537 B2 | 5/2012 | Refai et al. | |
| 8,920,502 B1 * | 12/2014 | Muhanna | A61F 2/44 623/17.16 |
| 2001/0014826 A1 | 8/2001 | Biedermann et al. | |
| 2002/0068978 A1 | 6/2002 | Camino et al. | |
| 2002/0082695 A1 | 6/2002 | Neumann | |
| 2002/0138142 A1 | 9/2002 | Castro et al. | |
| 2002/0161441 A1 | 10/2002 | Lang et al. | |
| 2003/0078660 A1 | 4/2003 | Clifford et al. | |
| 2003/0083746 A1 | 5/2003 | Kuslich | |
| 2004/0049271 A1 | 3/2004 | Biedermann et al. | |
| 2004/0098128 A1 | 5/2004 | Biedermann et al. | |
| 2004/0172129 A1 | 9/2004 | Schafer et al. | |
| 2004/0225360 A1 | 11/2004 | Malone | |
| 2004/0259972 A1 | 12/2004 | Ringeisen et al. | |
| 2005/0159814 A1 | 7/2005 | Karahalios | |
| 2005/0209697 A1 | 9/2005 | Paponneau et al. | |
| 2005/0234550 A1 | 10/2005 | Metz-Stavenhagen | |
| 2006/0058879 A1 * | 3/2006 | Metz-Stavenhagen | A61F 2/44 623/17.15 |
| 2006/0074490 A1 | 4/2006 | Sweeney | |
| 2006/0200244 A1 | 9/2006 | Assaker | |
| 2007/0179610 A1 | 8/2007 | Biedermann et al. | |
| 2007/0255408 A1 * | 11/2007 | Castleman | A61F 2/44 623/17.11 |
| 2009/0036985 A1 | 2/2009 | Whiting | |
| 2012/0265303 A1 | 10/2012 | Refai et al. | |

FOREIGN PATENT DOCUMENTS

| | | |
|---|---|---|
| EP | 1 080 703 A2 | 3/2001 |
| EP | 1 080 703 B1 | 11/2004 |
| JP | 2002-238929 A | 8/2002 |
| JP | 2004-537372 A | 12/2004 |
| WO | WO 02/09626 A1 | 2/2002 |

OTHER PUBLICATIONS

Final Office action for U.S. Appl. No. 11/645,228, dated Aug. 18, 2010, 9 pages.
European Search Report for European Application No. 060147393.4 dated Apr. 25, 2007, Place of Search—Munich, Date of Completion of Search—Apr. 17, 2007, 9 pages.
Office action for U.S. Appl. No. 13/914,471, dated Jun. 2, 2014, 9 sheets.
Office action dated Jan. 9, 2013 for U.S. Appl. No. 11/645,228, 8 pages.
Final Office Action for U.S. Appl. No. 13/914,471, dated Jan. 30, 2015 (8 pages).
Office Action for U.S. Appl. No. 15/012,827, dated Jul. 13, 2016 (14 pages).
Final Office Action for U.S. Appl. No. 15/012,827, dated Oct. 31, 2016 (11 pages).

* cited by examiner

SPACER FOR INSERTION BETWEEN TWO VERTEBRAE

CROSS-REFERENCE TO RELATED APPLICATION(S)

This application is a continuation of U.S. patent application Ser. No. 12/856,061, filed Aug. 13, 2010, which is a continuation of U.S. patent application Ser. No. 11/776,409 filed Jul. 11, 2007, now U.S. Pat. No. 7,803,191, which claimed the benefit of the filing date of U.S. Provisional Application No. 60/830,809, filed Jul. 14, 2006 and claims priority from European Patent Application Number EP 06014739.4, filed Jul. 14, 2006, the disclosures of which are incorporated fully herein by reference.

BACKGROUND

The present application relates to a spacer for insertion between two vertebrae. In particular, the present application relates to a spacer with adjustable axial length which can be filled with bone graft after insertion between the vertebrae.

A spacer with adjustable axial length is known from U.S. Pat. No. 6,200,348. The spacer comprises a first sleeve-shaped member and a second member which is slidably guided within the first member for adjusting the overall length of the spacer. The adjustment of the axial length is made by means of ratchet notches provided at the outer wall of the second member and an engagement member provided at the first member. The spacer has a plurality of openings in its wall which allows insertion of bone cement and growing-in of blood vessels.

Usually the spacer is either filled with bone cement through infusion after insertion between the vertebrae or it is filled with bone material, in particular with bone graft, through the open ends of the tubular spacer before it is implanted into a patient's body. The length of the known spacer can be adjusted after the spacer is inserted between two vertebrae. In certain situations it is desirable to add or remove bone material to or from the interior of the spacer after adjusting the axial length of the spacer.

U.S. Pat. No. 6,616,695 B1 describes a spacer for insertion between two vertebrae the axial length of which can be adjusted. The spacer comprises a first tubular part having a threaded inner surface and a second tubular part having a threaded outer surface, said parts forming a screw-nut connection which allows adjustment of the axial length of the spacer. The first tubular part has a plurality of circular openings in its wall. The second tubular part has a plurality of elongate openings in its wall. The length of the spacer can be adjusted by turning the parts relative to each other. This requires more space than a sliding motion for adjusting the length. Furthermore, the vertebral body can be damaged by the toothed end plate of the spacer during the turning motion. The elongate openings serve for insertion of a fixing screw. The openings in the wall are too small for inserting bone graft.

U.S. Pat. No. 5,290,312 describes a prosthetic vertebra with adjustable axial length comprising a first hollow parallelepiped-shaped component and a second hollow parallelepiped-shaped component which can slide in the first component. Each component has an abutting end surface for abutting a vertebra and an anchoring window formed in the abutting end. Also, each component has an open first side which establishes an access window and an open end formed opposite the abutting end. The spacer comprises means for preventing slidable motion between the components to establish a desired length. To connect the spacer with the vertebrae, pliable bone cement is infused into the components through the access window which flows out of the anchor windows and hardens. Since each component has an open side, bone graft which would be inserted through this side can easily fall out. Furthermore, the open side leads to a reduced stability.

U.S. Pat. No. 6,524,341 B2 also discloses spacer with adjustable length. A turning motion is necessary for expansion and retraction of the parts of the spacer relative to each other.

U.S. Pat. No. 6,176,881 B1 discloses a spacer with adjustable length. The spacer comprises an interior hollow body and an exterior hollow body, the interior body has a catch mechanism on its outer surface and the exterior body includes an elastic element which latches onto the catch mechanism thereby fixing the length of the spacer in such a way that it is resistant to compression. If a blocking of the hollow bodies against expansion is desired, a locking screw is used which is arranged on one side of the spacer. If the length of the spacer shall be reduced again, the elastic element is actuated with a tool acting on the opposite side of the spacer. A spacer similar to that disclosed in U.S. Pat. No. 6,176,881 B1 is known under the trade name Synex. This spacer additionally has an access opening for introduction of bone graft. Based on the above, there is a need for a spacer for insertion between two vertebrae which can be adjusted in length and which can be filled in situ not only with bone cement but also with bone graft and which has an improved handling.

SUMMARY

The spacer of the present application can be filled with bone graft before insertion between two vertebrae as usual. After inserting the spacer between the vertebrae and adjusting the axial length additional bone graft can be introduced through the access opening. Alternatively, all bone graft can be inserted after insertion of the spacer between the vertebrae and adjustment of the length.

The spacer of the present application can be expanded by a sliding motion which requires less space and time for the operation compared to an expansion by means of a rotational motion.

The access opening has a closed rim which results in higher mechanical stability of the spacer compared to an access window with an open side.

The length adjusting elements and the length fixation elements are accessible from the same side of the spacer. This leads to an improved handling. In addition, the access opening, the length adjusting and the length fixation elements can be accessed from one side allowing for MIS (minimally invasive surgery) or MOS (mini open surgery) approaches.

The end section of the spacer can be formed as a multiple cage structure. This provides an enhanced fixation in the vertebra due to a larger contact area and a reduced depth of penetration into the bone at the contact area thus reducing damage of the adjacent vertebra. The contour of the outer cage of the multiple case structure can be adapted to the contour of the surface of the vertebral body.

The spacer can be manufactured from tubes which is more simple to manufacture than other shapes.

Further advantages will become apparent from the description of the embodiment in conjunction with the accompanying drawings.

DETAILED DESCRIPTION

As can be seen from FIGS. 1 to 6, the spacer 1 according to one embodiment comprises a first cylindrical tubular member 2 and a second cylindrical tubular member 3. The outer diameter of the second tubular member 3 is chosen to allow a sliding guidance of the second tubular member 3 in the first tubular member 2.

Figure 1:
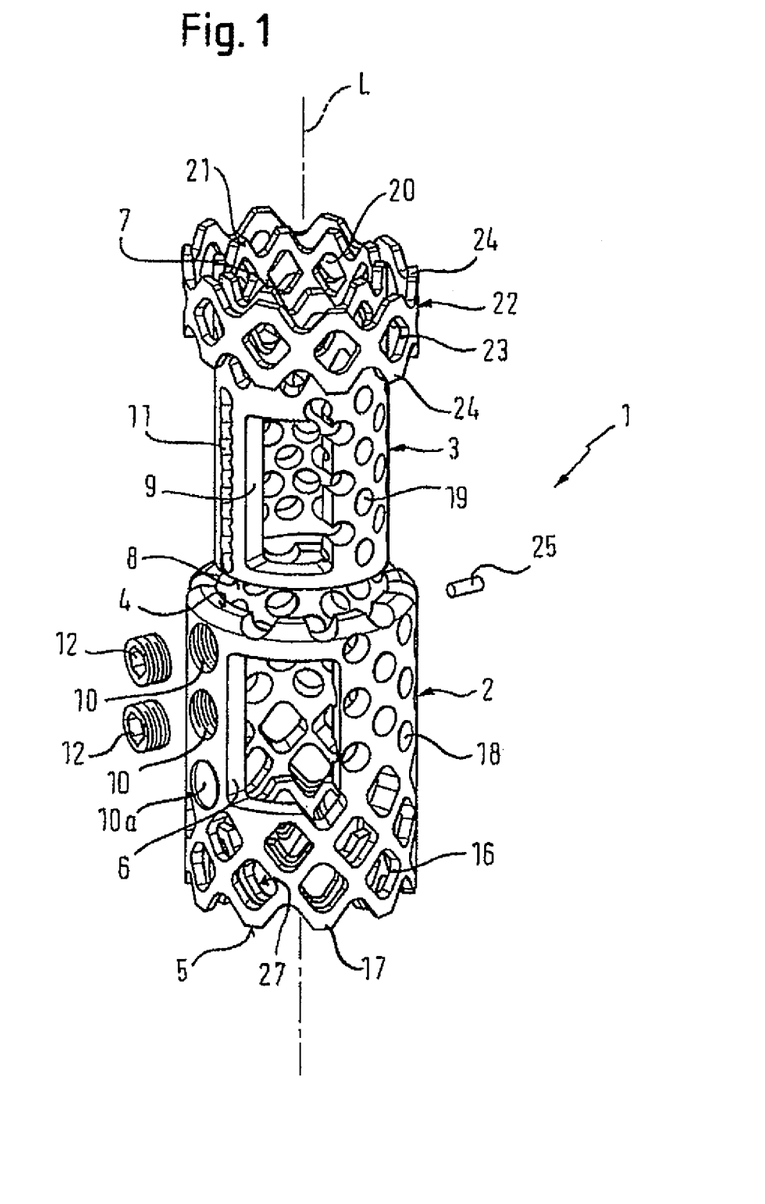
FIG. 1 shows a perspective exploded view of an embodiment of the spacer.

The first tubular member 2 has a first end 4, an opposite second end 5 and a hollow interior surrounded by the wall of the tube. In the wall at a predetermined distance from the first end 4 an access opening 6 is provided which extends over approximately half of the length of the first tubular member 2. In the embodiment shown the access opening is a rectangular opening. The length of the long side of the rectangle is approximately half of the length of the first tubular member 2 and the length of the short side is approximately a quarter of the length of the first tubular member 2. The dimension of the access opening 6 is such that natural bone graft can be filled in and removed from the opening during or after surgery.

Similarly the second tubular member has a first end 7 and an opposite second end 8, a hollow interior and wall defined by the tube. At a distance from the second end an access opening 9 is provided in the wall of the second tubular member. The access opening 9 extends over approximately half of the length of the second tubular member 3. In the embodiment shown, the access opening 9 has a rectangular shape with the same dimensions as the access opening 6 of the first tubular member. In an assembled state as shown in FIG. 2, the second tubular member 3 is inserted in the first tubular member 2 in such a way that the access opening 6 of the first tubular member and the access opening 9 of the second tubular member are aligned in a radial direction.

Since the access opening of each of the tubular members is provided at the distance from the first end and the second end, respectively, the access openings are separated from the first or the second end, respectively, by a part of the wall and therefore have a closed rim.

The position of the second tubular member 3 relative to the first tubular member 2 in a direction of the longitudinal axis L of the spacer can be fixed by a locking structure. The locking structure is formed by a plurality of threaded openings 10 aligned in an axial direction in the wall of the first tubular member 2. The threaded openings 10 are arranged at one side of the access opening 6 and close to the access opening in such a way that the threaded openings are accessible by the surgeon during surgery from the same side as the access opening. Further, the locking structure comprises a plurality of spherical segment-shaped recesses 11 which are arranged in a line in the direction of the longitudinal axis L of the spacer in the outer surface of the wall of the second tubular member 3. The recesses 11 are formed side by side and have a depth less than the radius thereof The line of recesses 11 is arranged on one side of the access opening 9 of the second tubular member 3 and close to the access opening 9 in such a way that in the assembled state as shown in FIGS. 2 and 3 the line of threaded openings 10 matches with the line of the recesses 11. The locking structure further comprises locking screws 12 which can be screwed into the threaded openings 10. The locking screw 12 has on one side a spherical segment-shaped projection 13 which fits into the spherical segment-shaped recesses 11. On the opposite side, the locking screw 12 has a recess for engagement with a screwing-in tool. The line of recesses 11 extends at least over the same length as the line of threaded openings 10. An unthreaded opening 10a can be provided in the line of threaded openings for engagement with a holding tool (not shown).

Figure 2:
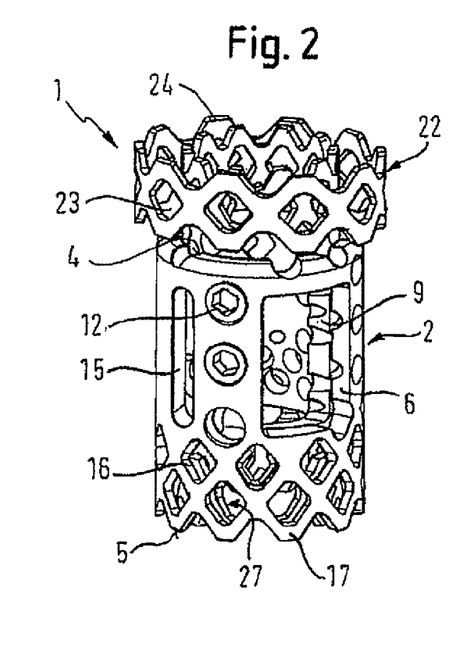
FIG. 2 shows a side perspective view of the spacer in an assembled state with an axial length near the minimum possible length.
Figure 3:
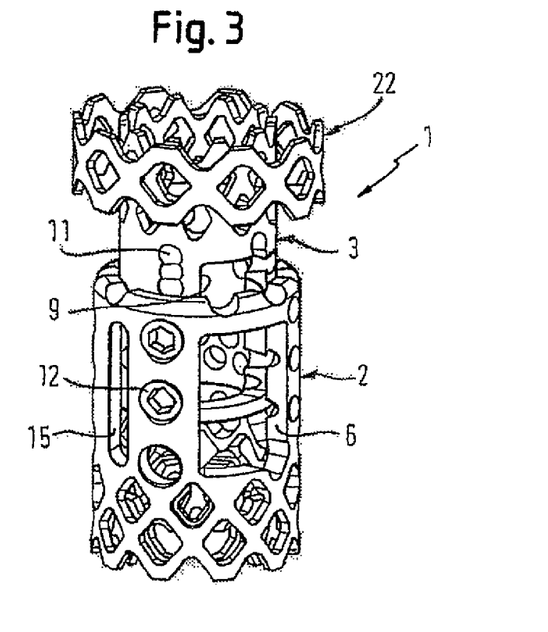
FIG. 3 shows a side perspective view of the spacer in an assembled extended state having a greater length than shown in FIG. 2.
Figures 12, 13:
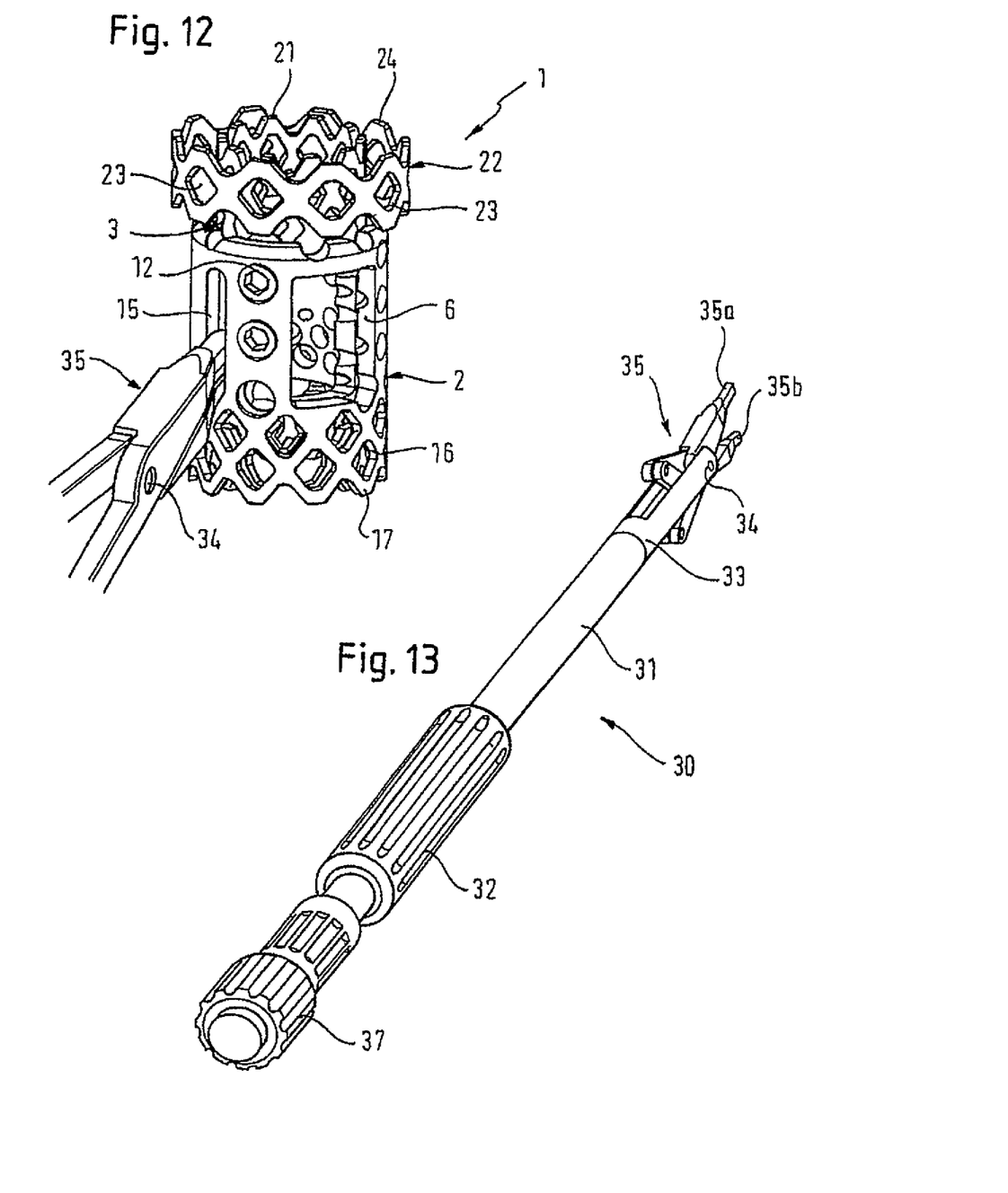
FIG. 12 shows a perspective side view of the spacer engaged with a length adjustment tool.
FIG. 13 shows a perspective view of the length adjustment tool.

As can be seen in FIGS. 2,3 and 12, the first tubular member 2 comprises an elongate opening 15 which extends from a distance from the first end 4 to a distance from the second end 5. The elongate opening 15 has a length which is approximately the same length as the access opening 6 and has a width which is considerably smaller than the width of the access opening 6 in such a way that a bone graft cannot pass through the elongate opening 15. Further, the first tubular member 2 comprises a plurality of diamond-shaped openings 16 which are arranged in a region adjacent to the second end 5. The diamond-shaped openings 16 have a size which is smaller than the size of the access opening 9 in such a way that bone graft cannot pass through the diamond-shaped openings. The diamond-shaped openings 16 are arranged in circumferential rows wherein one row is offset from the adjacent row by half a diamond height in axial direction. The row of diamond-shaped openings 16 which is closest to the second end 5 is cut so that the openings are open to the second end 5 forming prongs 17 for engagement with the adjacent vertebra.

Figure 4:
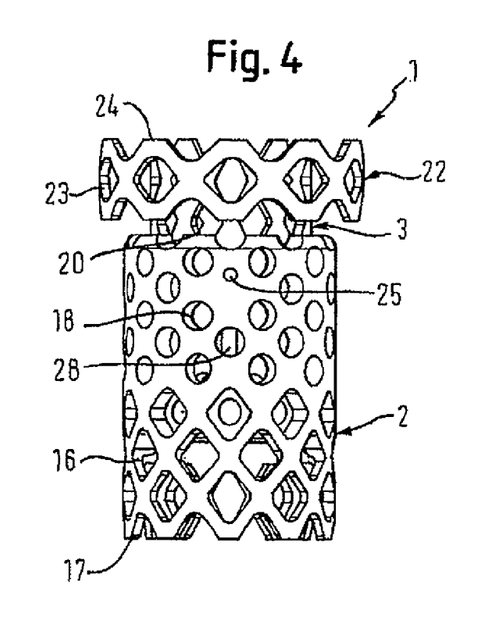
FIG. 4 shows a side view of the spacer of FIG. 2.
Figure 5:
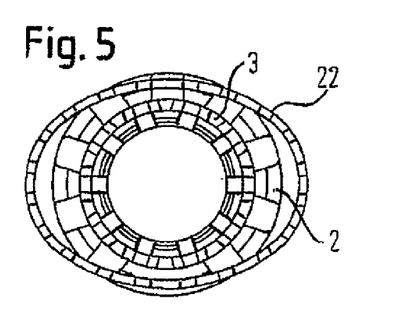
FIG. 5 shows a top view of the spacer of FIG. 2.
Figure 6:
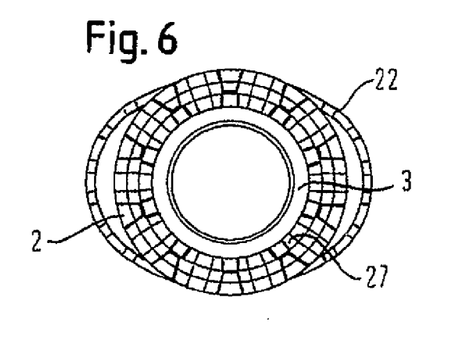
FIG. 6 shows a bottom view of the spacer of FIG. 2.

As can be seen in particular from FIGS. 1 and 4, the first tubular member 2 additionally comprises a plurality of circular openings 18 in a region starting at the first end 4. The circular openings 18 have a size which does not allow introduction and removal of bone graft. The diamond-shaped openings 16 and the circular openings 17 serve for allowing in-growth of blood vessels and tissue.

Similarly, the second tubular member 3 comprises adjacent to its second end 8 a plurality of circular openings 19 and adjacent to the first end 7 a plurality of diamond-shaped openings. The circular openings 19 and the diamond-shaped openings 20 are sized so that bone graft cannot be introduced or removed through these openings. Similar to the first tubular member 2 the row of diamond-shaped openings 20 which is nearest to the first end 7 of the second tubular member is cut so as to form prongs 21 for engagement with the vertebral body.

As can be seen in FIG. 1 and 4, a pin 25 is provided which can be fixed for example to the first tubular member 2 and guided in an elongate slit 28 (FIG. 4) provided in the second tubular member 3 to prevent rotation and forming a stop to prevent separation of the first and the second tubular member.

Figures 7, 9:
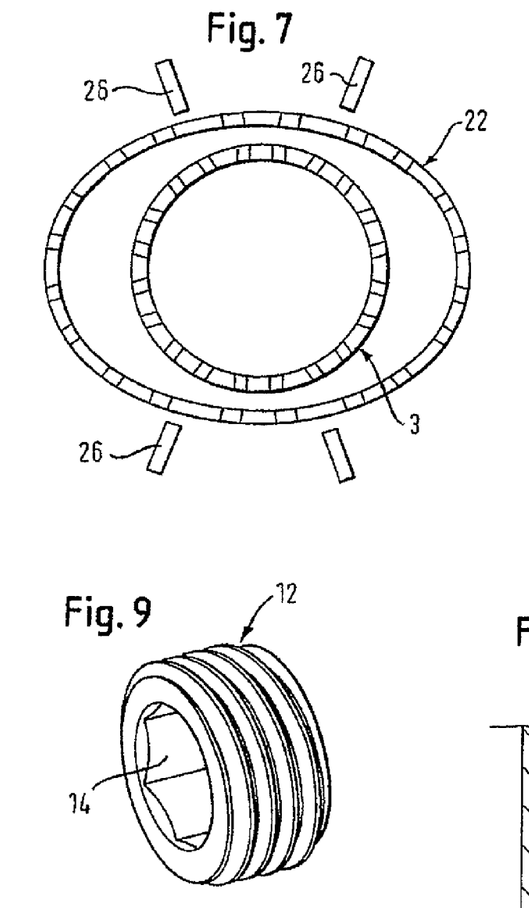
FIG. 7 shows a schematic exploded representation of the end section of the spacer according to a first example seen from the top.
FIG. 9 shows a perspective view of a locking element.
Figure 8:
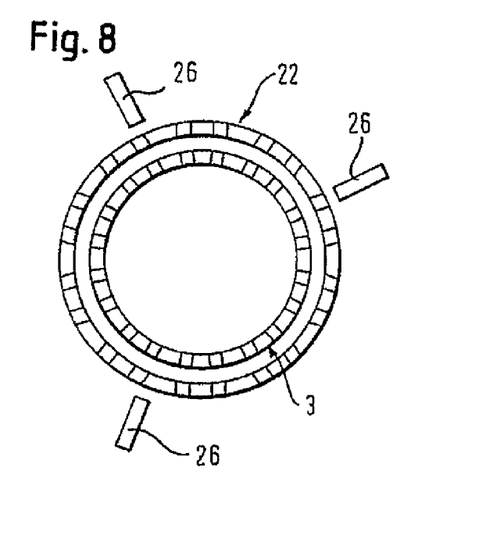
FIG. 8 shows a schematic exploded representation of the end section of the spacer according to a second example seen from the top.
Figure 10:
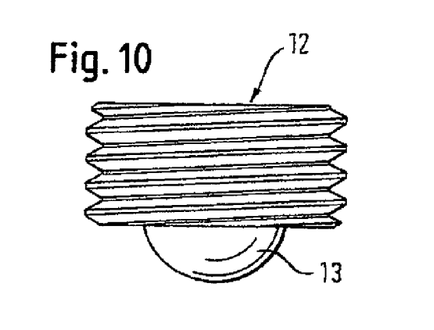
FIG. 10 shows a side view of the locking element of FIG. 10.
Figure 11:
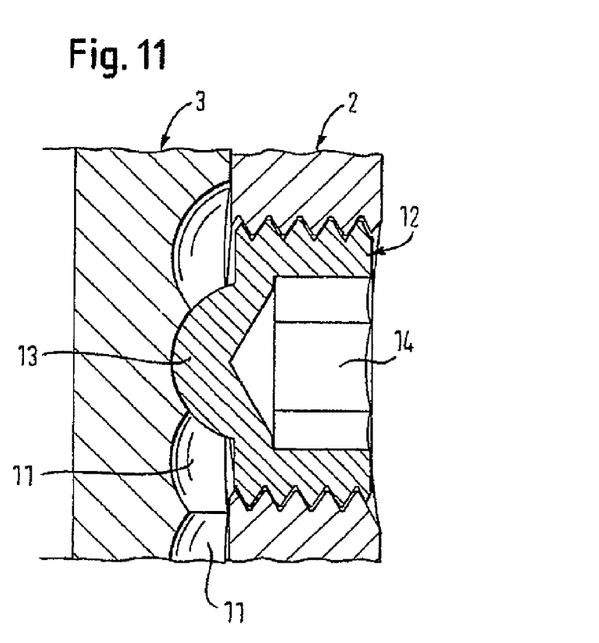
FIG. 11 shows a sectional view of the locking structure to fix the axial length of the spacer.

The spacer further comprises a third tubular member 22 the axial length of which is approximately the axial length of the region of the second tubular member in which the diamond-shaped openings 20 are located. The third tubular member 22 also comprises diamond-shaped openings 23 in its wall and prongs 24 at both free ends. The third tubular member 22 is fixedly connected to the second tubular member by means of pins 26 as shown in the schematic exploded representation in FIGS. 7 and 8, or with screws, rivets or the like. The third tubular member 22 can have an oval-shaped cross section as shown in FIG. 7 or a circular cross section as shown in FIG. 8. The third tubular member and the end section of the second tubular member form a double cage structure which enhances the area of contact with the vertebra compared to the area of contact of only the second tubular member. Since the outer diameter of the second tubular member is smaller than that of the first tubular member, the third tubular member can be used to enlarge the contact area and to adapt the shape of the ring of prongs to the contour of the end surface of the vertebral body which shall be engaged.

As can be seen from FIGS. 1 to 6, a fourth tubular member 27 which is similar to the third tubular member 22 is provided inside the first tubular member 2 at its free second end 5 and is attached to the first tubular member 2 to form a double cage structure. The fourth tubular member 27 also comprises diamond-shaped openings and prongs for attachment to the bone.

In an assembled state the elongate opening 15 covers at least one of the circular openings 19 or the diamond-shaped openings 20 of the second tubular member 3. The elongate opening of the first tubular member and one of the circular or diamond-shaped openings of the second tubular member form an example of a length adjusting structure which allows expansion and compression of the two tubular members relative to each other when being engaged with a tool.

In the embodiment shown, the access opening, the locking structure and the length adjusting structure are arranged in the assembled state within approximately one half or less of the circumference of the spacer.

A length adjustment tool for telescoping the second tubular member 3 relative to the first tubular member 2 is shown in FIGS. 12 and 13. The tool 30 comprises a tube 31 with a handle 32 at one end and a fork-shaped section 33 at the other end. A rotation axis 34 bridges the fork-shaped section 33 at the free end. A scissor-like structure 35 is pivotably connected with the fork-shaped section 33. The scissor-like structure 35 can pivot around the axis 34. It comprises arms 35a and 35b which can be moved between a folded position and an unfolded position. One of the arms is structured to engage with the elongate opening 15 of the first tubular member 2 and the other arm is structured to engage with one of the circular or diamond-shaped openings of the second tubular member 3.

The tool further comprises a bar with a handle 37 at its free end. The bar is accommodated in the tube 31 and extends into the fork-shaped section 33. By rotating the bar with the handle 37, the scissor-like structure 35 is moved so that the arms 35a and 35b open or close, respectively.

In use, first the spacer is filled with bone graft before inserting it between the vertebrae. The spacer has its minimum length. Then, the spacer is inserted between two adjacent vertebrae, for example after removal of a vertebra to bridge the space. Then, the length of the spacer is adjusted by telescoping the second tubular member out of the first tubular member. The movement is a sliding movement without rotation. The tool shown in FIGS. 12 and 13 is used in such a way that the scissor-like structure is inserted into the elongate hole 15 in the first tubular member with one arm 35a and engaging one of the holes 19 or 20 of the second tubular member with the other arm 35b. By rotating the bar the scissor-like structure pivots and the second tubular member is telescoped out of the first tubular member. When the desired length is achieved, the locking screws 12 are inserted into the threaded openings 10 until the spherical segment-shaped projection engages with one of the spherical segment shaped recesses 18. Since the access openings of the first tubular member and the second tubular member, respectively, are aligned, the spacer has still openings large enough to insert bone graft. Then, additional bone graft is inserted to fill out completely the interior of the spacer.

Since the locking structure and the elongate opening 15 which serves for expansion or compression are located on the same side, the spacer can be quickly adjusted to its desired axial length and fixed in this position. Since the access openings of the first and the second tubular member are on the same side close to the locking structure, it is possible to quickly fill in bone graft during surgery.

The spacer can be coated for enhancing in-growth of blood vessels or tissue. The spacer can be coated with different materials on the outer surface and the inner surface of the tubular members, respectively. The first and the second tubular member can be coated with different materials.

Modifications of the embodiment shown are possible. The access opening needs not to have a rectangular shape. It can have any shape provided that it is large enough to allow the insertion of bone graft. More than one elongate opening 15 can be provided.

The circular openings and the diamond-shaped openings can be omitted or can have any other shape, provided that they are small enough not to allow removal or insertion of bone graft. In this case, instead of an opening of the second tubular member for engagement with the tool, another surface structure can be provided on the second tubular member.

The locking structure also can be modified. The spherical-shaped recesses 11 can be provided at the inner wall of the first tubular member and the threaded openings can be provided in the wall of the second tubular member. The locking screw is then screwed from the hollow interior into the threaded openings.

The tubular members are shown with a circular cross section. However, any other shape of the cross section is possible. For example, the shape of the cross section of the tubular members can be adapted to the contour of the end surface of a vertebral body.

The third tubular member and the fourth tubular member also can have a cross section which is different from a circular cross section or an oval-shaped cross section.

Further tubular members can be attached to the end section of the first and/or the second tubular member to provide a multi-cage structure. Alternatively, the third and fourth tubular member can be omitted.

While particular forms of the disclosure have been illustrated and described, it will be apparent that various modifications can be made without departing from the spirit and scope of the disclosure. Accordingly, it is not intended that the disclosure be limited, except as by the appended claims.

What is claimed is:

1. A spacer for insertion between vertebrae, said spacer having a variable axial length and comprising:
   a first, member having a hollow interior, a tubular wall, and a longitudinal axis;
   a second member having a hollow interior and a tubular wall, the second member being slidable within the first member along a first length an axial direction adjusting an overall length of the spacer; and
   a length adjustment structure comprising an elongate opening extending in the axial direction in the wall of one of the first member or the second member and an engagement structure on the well of the other of the first member or the second member, the elongate opening having a length in the axial direction greater than a width in a direction transverse to the axial direction, the elongate opening and the engagement structure overlapping with each other and being respectively configured to receive and engage respective ones of pivotably connected arms of a tool to adjust the overall length without rotating the second member relative to the first member, an outer perimeter size of the second member being smaller than an inner perimeter size of the first member along the first length such that the second member is freely slidable within the first member along the first length in both directions of the longitudinal axis when the elongate opening and the engagement structure overlap with each other,
   wherein at least the first member or the second member comprises an access opening in its wall, the access opening having a size which is adapted for inserting bone graft through the access opening into the interior, and wherein the width of the elongate opening is less than a width of the access opening in the direction transverse to the axial direction.

2. The spacer according to claim wherein the access opening and the length adjustment structure are arranged so as to be accessible from a same side of the spacer.

3. The spacer according to claim 2, further comprising a locking structure for fixing the overall length, and wherein the access opening, the length adjustment structure and the locking structure are arranged so as to be accessible from the same side of the spacer.

4. The spacer according to claim 1, wherein the access opening is sized to allow an in vivo introduction of bone graft.

5. The spacer according to claim 1, wherein the length of the elongate opening is at least about half of a length of the wall of the one of the first member or the second member in the axial direction.

6. The spacer according to claim wherein the elongate opening extends in the well of the first member and the engagement structure is on the wail of the second member.

7. The spacer according to claim 1, wherein one of the first member or the second member comprises an assembly pin, and the other of the first member or the second member comprises an elongate slit elongated in the axial direction, and the elongate slit mates with and guides the assembly pin therein to be movable relative thereto in the axial direction in order to maintain the second member in a slidable orientation within the first member.

8. The spacer according to claim 7, wherein the first member comprises the assembly pin, and the second member comprises the elongate slit.

9. The spacer according to claim 1, wherein the engagement structure defines a hole in the wall of the other of the first member or the second member.

10. The spacer according to claim 1, wherein the second member comprises the access opening, and the access opening has an entirely closed rim around the access opening.

11. The spacer according to claim 10, wherein the first member comprises another access opening, and the another access opening has an entirely closed rim around the another access opening.

12. A spacer for insertion between two vertebrae, the spacer comprising:
   a first member having a hollow interior and a tubular wall, the tubular wall having a longitudinal axis extending between a first end and a second end of the tubular wall;
   a second member having a hollow interior and a tubular wall, the second member being slidable within the first member along the longitudinal axis for adjusting an overall length of the spacer;
   a length adjustment structure comprising an opening in the wall of first member extending along a direction of the longitudinal axis and a structure in the wall of the second member configured to engage a tool inserted through the opening of the first member for telescoping the second member relative to the first member to adjust the overall length; and
   a locking structure for fixing the overall length, the locking structure comprising a plurality of recesses arranged in a line extending in the direction of the longitudinal axis in the wall of one of the first member or the second member and a locking screw at the other of the first member or the second member and configured to engage with a recess of the plurality of recesses to fix the overall length, wherein surfaces of adjacent recesses of the plurality of recesses intersect each other,
   wherein at least one of the first members and the second member includes an access opening configured for inserting bone graft.

13. The spacer according to claim 12, wherein the adjacent recesses overlap each other in the axial direction.

14. The spacer according to claim 12, wherein the recesses are unthreaded.

15. The spacer according to claim 12, wherein the locking screw comprises a projection configured to be received in the recess to fix the overall length.

16. The spacer according to claim 12, wherein the plurality of recesses extends in the wall of the second member and the locking screw is arranged at the first member.

17. The spacer according to claim 12, wherein one of the first member or the second member comprises an assembly pin, and the other of the first member or the second member comprises an elongate slit elongated in the direction of the longitudinal axis, and the elongate slit mates with and guides the assembly pin therein to be movable relative thereto in the direction of the longitudinal axis to maintain the second member in a slidable orientation within the first member.

18. The spacer according to clam 17, wherein the first member comprises the assembly pin, and the second member comprises the elongate slit.

19. The spacer according to claim 12, wherein the opening in the wall of the first member of the length adjustment structure is an elongate opening having a length in the direction of the longitudinal axis greater than a width in a direction transverse to the direction of the longitudinal axis.

20. The spacer according to claim 12, wherein the second member is freely slidable within the first member along both directions of the longitudinal axis.

21. The spacer according to claim 12, wherein the opening in the wall of the first member of the length adjustment structure and the structure in the wall of the second member of the length adjustment structure overlap with each other.

\* \* \* \* \*

UNITED STATES PATENT AND TRADEMARK OFFICE
CERTIFICATE OF CORRECTION

PATENT NO. : 9,744,051 B2
APPLICATION NO. : 14/532647
DATED : August 29, 2017
INVENTOR(S) : Lutz Biedermann et al.

Page 1 of 2

It is certified that error appears in the above-identified patent and that said Letters Patent is hereby corrected as shown below:

On the Title Page (57) Abstract, Column 2, Line 4

Delete "tubular wall the second",
Insert --tubular wall, the second--

(56) References Cited, Other Publications pg. 2, Column 2, Line 5

After "April 17, 2007",
Insert --Examiner - Stefan Josten--

In the Specification

Column 4, Line 18

Delete "thereofThe",
Insert --thereof. The--

Column 4, Line 34

Delete "FIGS. 2,3 and 12,",
Insert --FIGS. 2, 3 and 12,--

Column 4, Line 59

Delete "circular openings 17",
Insert --circular openings 18--

Column 6, Line 20

Delete "shaped recesses 18.",
Insert --shaped recesses 11.--

In the Claims

Column 7, Line 8, Claim 1

Delete "between vertebrae",
Insert --between two vertebrae--

Signed and Sealed this
Ninth Day of October, 2018

Andrei Iancu
*Director of the United States Patent and Trademark Office*

CERTIFICATE OF CORRECTION (continued)
U.S. Pat. No. 9,744,051 B2

| | |
|---|---|
| Column 7, Line 10, Claim 1 | Delete "first, member", Insert --first member-- |
| Column 7, Line 14, Claim 1 | Delete "length an axial", Insert --length in an axial-- |
| Column 7, Line 14, Claim 1 | Delete "direction adjusting", Insert --direction for adjusting-- |
| Column 7, Line 19, Claim 1 | Delete "the well of the other", Insert --the wall of the other-- |
| Column 7, Line 42, Claim 2 | Delete "claim wherein", Insert --claim 1, wherein-- |
| Column 7, Line 57, Claim 6 | Delete "claim wherein", Insert --claim 1, wherein-- |
| Column 7, Line 58, Claim 6 | Delete "the well of the first", Insert --the wall of the first-- |
| Column 7, Line 59, Claim 6 | Delete "the wail of the second", Insert --the wall of the second-- |
| Column 8, Line 24, Claim 12 | Delete "wall of first", Insert --wall of the first-- |
| Column 8, Line 39, Claim 12 | Delete "first members and", Insert --first member and-- |
| Column 8, Line 60, Claim 18 | Delete "clam 17,", Insert --claim 17,-- |